United States Patent [19]

Yamaguchi

[11] Patent Number: 5,610,527
[45] Date of Patent: Mar. 11, 1997

[54] PHASE DIFFERENCE MICROWAVE DENSITOMETER AND METHOD WHICH DETECTS A NUMBER OF PHASE ROTATIONS THROUGH A REFERENCE POINT

[75] Inventor: Seiji Yamaguchi, Sagamihara, Japan

[73] Assignee: Kabushiki Kaisha Toshiba, Kawasaki, Japan

[21] Appl. No.: 392,745

[22] PCT Filed: Jul. 12, 1994

[86] PCT No.: PCT/JP94/01138

§ 371 Date: Mar. 8, 1995

§ 102(e) Date: Mar. 8, 1995

[87] PCT Pub. No.: WO95/02815

PCT Pub. Date: Jan. 26, 1995

[30] Foreign Application Priority Data

Jul. 12, 1993 [JP] Japan .................................. 5-171576

[51] Int. Cl.$^6$ .......................... G01R 27/32; G01N 22/00
[52] U.S. Cl. ............................................................ 324/639
[58] Field of Search ........................ 342/127; 324/76.82, 324/76.77, 644, 639–645; 364/484; 367/90; 73/602, 601, 32 R, 32 A, 24.05, 24.06, 30.01, 30.04

[56] References Cited

U.S. PATENT DOCUMENTS

| 3,626,284 | 12/1971 | Bak ........................................ 324/642 |
| 4,727,311 | 2/1988 | Walker .................................. 324/640 |
| 4,947,127 | 8/1990 | Helms et al. ......................... 324/640 |
| 5,502,393 | 3/1996 | Yamaguchi et al. ................. 324/639 |

FOREIGN PATENT DOCUMENTS

| 0300826 | 1/1989 | European Pat. Off. . |
| 52-109892 | 9/1977 | Japan . |
| 57-130572 | 7/1982 | Japan . |
| 58-22922 | 2/1983 | Japan . |
| 63-140948 | 6/1988 | Japan . |
| 2-5402 | 12/1990 | Japan . |
| 5-113412 | 5/1993 | Japan . |

OTHER PUBLICATIONS

Patent Abstracts of Japan, vol. 8, No. 113 (P–276), May 26, 1984, JP-A-59 019846, Feb. 1, 1984.

IBM Technical Disclosure Bulletin, vol. 16, No. 7, pp. 2204–2208, Dec. 1973, R.L. Comstock, et al., "Quadrature Servo Signal Utilizing A PlO Time Detection System".

Conference Proceedings IEEE Southeastcon '82, pp. 510–513, Apr. 4–7, 1982, A. Sodeifi, et al., "A Wide-Range Phase Detector".

Proceedings 5th Symposium On Engineering Problems of Fusion Research, pp. 654–657, Nov. 5–9, 1973, W.P. Ernst, "A Direct Readout, Self-Calibrating, Multi-Radian Microwave Phase Measuring System".

*Primary Examiner*—Hezron E. Williams
*Assistant Examiner*—Rose M. Miller
*Attorney, Agent, or Firm*—Oblon, Spivak, McClelland, Maier & Neustadt, P.C.

[57] ABSTRACT

A phase difference measuring apparatus obtains a first receive signal by transmitting and receiving a to-be-measured material in a reference state and a second receive signal by transmitting and receiving a signal wave to and from that material in a measured state. The apparatus finds a reference phase difference $\theta_1$ from the transmit wave and first receive signal and an apparent phase difference $\theta_{2'}$ from the transmit wave and second receive signal. The apparatus adds the apparent phase difference $\theta_{2'}$ to a product of the number of rotations, n, the apparent phase difference $\theta_{2'}$ passes through a given reference point and an angle of 360° to find a true phase difference $\theta_2$. The apparatus varies the number of rotations, n, to n+1 when the apparent phase difference $\theta_{2'}$, while being increased, passes through the reference point and that number of rotations, n, to n=n−1 when the apparent phase difference $\theta_{2'}$, while being decreased, passes through the reference point.

2 Claims, 10 Drawing Sheets

PHASE DIFFERENCE MICROWAVE DENSITOMETER AND METHOD WHICH DETECTS A NUMBER OF PHASE ROTATIONS THROUGH A REFERENCE POINT

TECHNICAL FIELD

The present invention relates to an apparatus and method for measuring a physical amount, such as the density of a suspended material contained in a measuring fluid and a distance to an object, and a chemical amount, such as the density of a chemical material dissolved in the measuring fluid, with the use of an electromagnetic wave, such as a light wave and radio wave, or an ultrasonic wave.

BACKGROUND ART

As a densitometer capable of measuring not only the density of a suspended material in a measuring fluid but also a material dissolved in a measuring fluid without involving the deposition of any suspended material on the inner wall of a density measuring tube, a type has been known which measures such a density with the use of a microwave. This type of densitometer is known in JPN PAT APPLN KOKAI PUBLICATION 59-19846.

Figure 14:
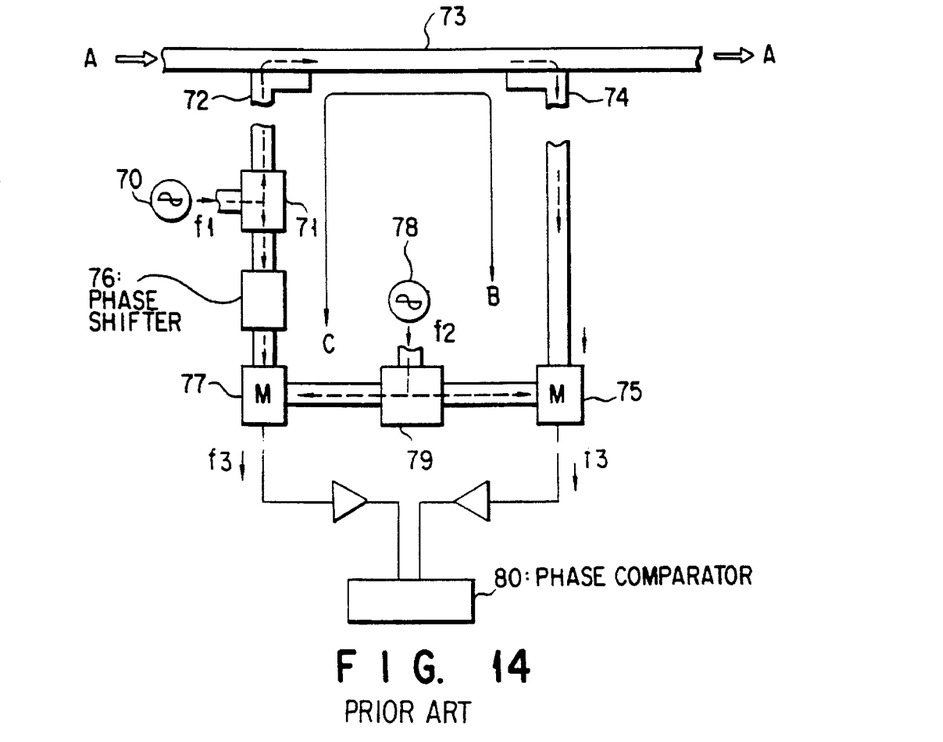
FIG. 14 is a diagrammatic view showing a densitometer to which a conventional phase difference measuring system is applied.

FIG. 14 shows an arrangement of a microwave densitometer as disclosed in the PUBLICATION above. In this meter, a microwave of a frequency f1 from a microwave oscillator 70 is separated by a distribute device 71 into two waves, one of which enters a density measuring tube 73 via one wave guide 72 provided on a density measuring tube 73. This branched wave passes through the measuring tube 73 and enters one mixer 75 via the other wave guide 74 provided on the measuring tube 73.

The other branched wave enters the other mixer 77 via a phase shifter 76. A microwave of frequency f2 from oscillator 78 enters these mixers 75 and 77 via a distribute device 79. These frequencies f1 and f2 are mixed at the mixers 75 and 77 and a low frequency signal is taken out as a frequency f3=f1−f2 and input to a phase comparator 80. The phase comparator 80 detects a phase difference between a low frequency signal coming from the mixer 75 and that coming from the mixer 77.

If the phase delay of a microwave passing through a path B is given by $\theta_1$ in a state in which a measuring fluid moves through the measuring tube 73 with a to-be-measured material not contained therein, then the phase delay of the phase shifter 76 is so set that the phase delay of the microwave passing through a path C coincides with $\theta_1$.

If the phase difference between the phase of the microwave passing through the path B and that of the microwave passing through the path C is measured, by the comparator 80, in a state in which a measuring fluid moves with a to-be-measured material contained in the measuring tube 73, then the phase delay of the microwave passing through the path B is represented as a value proportional to the density of the to-be-measured material contained in the measuring fluid.

If the density is measured by detecting the phase delay of the microwave varying in accordance with the state of the density of the to-be-measured fluid, then there is a possibility that inconvenience as will be set out below will occur.

Figure 15:
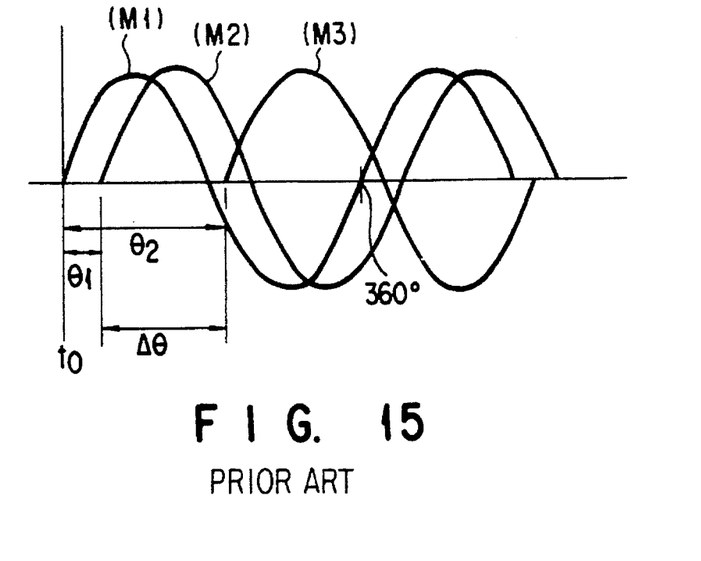
FIG. 15 is a view showing a phase delay of a microwave.

FIG. 15 shows a relation among a microwave (M1) before the phase is delayed by the phase shifter 76, a microwave (M2) phase-delayed with the phase shifter 76 and a microwave (M3) having a phase delay corresponding to the density of the measuring fluid passed through the path B.

Figure 16:
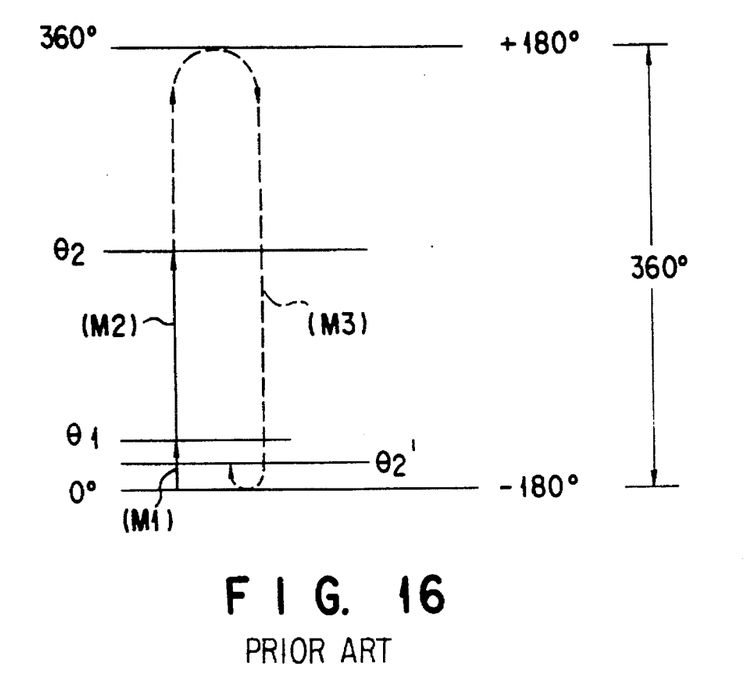
FIG. 16 is a view showing a rotation operation of an apparent phase delay angle.

The phase delay $\theta_2$ of the microwave (M3) relative to the microwave (M1) becomes greater in accordance with an increase in the density of the to-be-measured material. In the case where the density of the material is at a high level, there is a possibility that, as shown in FIG. 16, the phase delay $\theta_2$ will exceed 360°. Even if the phase delay $\theta_2$ exceeds 360°, an apparent (seeming) phase delay $\theta_{2'}$ lies between 0° and 360°.

In the case where a true phase delay $\theta_2$ (so called in distinct from an apparent phase delay $\theta_{2'}$.) falls within an angle range of $0° \leq \theta_2 < 360°$, it does not correspond to one rotation and that number of rotations, n, is called as n=0. In the case where the true phase delay $\theta_2$ falls within an angle range of $360° \leq \theta_2 < 720°$ after one rotation, that number of rotations, n, is called as n=1. In the case where the true phase delay $\theta_2$ varies in an opposite direction (minus direction) and falls within an angle range of $0° < \theta_2 \leq 360°$, that number of rotations, n, is called as n=−1. The number of rotations, n, varies similarly.

Since, in the phase comparator 80, the true phase delay $\theta_2$ is detected as an apparent phase delay $\theta_{2'}$, if the true phase delay $\theta_2$ corresponding to the density of the to-be-measured fluid exceeds 360°, a result of measurement reveals apparently a low density in spite of being a high level. In spite of the true phase delay $\theta_2$ being below 0°, on the other hand, a result of measurement reveals apparently a higher density than in actual practice.

With an increase in the transmission distance of a microwave in the measuring tube 73, the phase delay $\theta_2$ becomes greater in accordance with the length of the transmission distance, presenting a similar problem as set out above.

when the density of the fluid is so measured by detecting the phase delay of the microwave, the problem occurs as set out above. JPN PAT APPLN KOKAI PUBLICATION 2-238348 discloses a method for measuring a density whereby one solution to the problem is made. According to the technique as disclosed in this Publication, it is possible to detect the density of a to-be-measured fluid by measuring, by means of frequency modulation, a speed variation occurring upon passage of a microwave through a to-be-measured fluid.

Disclosure of the Invention

An object of the present invention is to provide an optimal phase difference measuring apparatus or a phase difference measuring method which can measure a physical amount or a chemical amount from a difference $\Delta\theta = \theta_2 - \theta_1$ between a phase difference $\theta_1$ between transmit and receive waves obtained by transmitting and receiving a signal wave to and from a to-be-measured object in a reference state and a phase difference $\theta_2$ between transmit and receive waves obtained by transmitting and receiving a signal wave to and from that object in a measuring state.

Another object of the present invention is to provide a phase difference measuring apparatus or a phase difference measuring method which can accurately measure a state (a physical amount or a chemical amount) of a to-be-measured material even if a phase difference O1 or O2 exceeds 360° or is below 0°.

Another object of the present invention is to provide a phase difference measuring apparatus or a phase difference measuring method which can readily realize a densitometer capable of accurately measuring a density in a high-density measuring fluid and accurately measuring a density in a measuring fluid flowing through a large-sized measuring tube.

Another object of the present invention is to provide a phase difference measuring apparatus or a phase difference measuring method which can readily realize a distance meter capable of accurately measuring a distance to a continuously moving material.

A phase difference measuring apparatus comprises:

a signal wave detecting unit for obtaining a first receive signal by transmitting and receiving a signal wave to and from a to-be-measured object in a reference state and a second receive signal by transmitting and receiving a signal wave to and from that to-be-measured material in a measuring state;

a phase detecting unit for finding a reference phase difference $\theta_1$ corresponding to a phase difference between the transmit signal wave and the first receive signal and an apparent phase difference $\theta_{2'}$ between the transmit wave and the second receive signal;

a phase difference correcting unit for adding the apparent phase difference $\theta_{2'}$ to a product between the number of rotations, n, the apparent phase deference $\theta_{2'}$ passes through a reference point 360° or 0° and an angle of 360° to find a true phase difference $\theta_2$, the reference point constituting one angle in a variation range (0° to 360°) of the apparent phase difference $\theta_{2'}$;

a tendency detecting unit for continuously detecting the direction in which the apparent phase difference $\theta_{2'}$ is increased or decreased;

a first rotation number varying unit for varying that number of rotations, n, to n=n+1 when the apparent phase difference $\theta_{2'}$ is detected by the tendency detecting unit as passing through the reference point while increasing;

a second rotation member varying unit for varying that number of rotations, n, to n=n−1 when the apparent phase difference $\theta_{2'}$ is detected by the tendency detecting means as passing through the reference point while decreasing; and a measured information outputting unit for outputting state-measured information of the to-be-measured material corresponding to an angle difference $\Delta\theta$ between the true phase difference $\theta_2$ and the reference phase difference $\theta_1$.

The present apparatus thus arranged varies that number of rotations, n, to n=n+1 each time the apparent phase difference between a transmit wave when a signal wave is transmitted and received to and from the to-be-measured material in a measuring state and a second receive signal passes through the reference point while increasing and varies that number of rotations, n, to n=n−1 each time the apparent phase difference $\theta_{2'}$ passes through the reference point while decreasing. The number of rotations, n, thus determined is multiplied by the angle 360° and the apparent phase difference $\theta_{2'}$ is added to the product n×360° to find a true phase difference $\theta_2$.

A phase difference measuring apparatus comprises:

a signal wave detecting unit for obtaining a first receive signal by transmitting and receiving a signal wave to and from a to-be-measured material in a reference state and a second receive signal by transmitting and receiving a signal wave to and from that material in a measuring state;

a phase detecting unit for finding a reference phase difference $\theta_1$ corresponding to a phase difference between the transmit wave as the signal wave and the first receive signal and an apparent phase difference $\theta_{2'}$ between the transmit wave and the second receive signal;

a phase difference correcting unit for adding the apparent phase difference $\theta_{2'}$ to a product between that number of rotations, n, the apparent phase difference $\theta_{2'}$ passes through a reference point and an angle of 360° to find a true phase difference $\theta_2$, the reference point constituting one angle in a variation range of the apparent phase difference $\theta_{2'}$;

an input unit for taking in the apparent phase difference $\theta_{2'}$ not continuously but at a predetermined time interval;

an upper area determining unit for setting an upper area in a given maximum-to-minimum angle range corresponding to a one rotation from the reference point and for determining whether or not the taken-in apparent phase difference $\theta_{2'}$ falls in the upper area containing that maximum angle;

a lower area determining unit for setting a lower area in that given minimum-to-maximum angle range and for determining whether or not the taken-in apparent phase difference $\theta_{2'}$ falls in the lower area containing that minimum angle;

a first rotation number varying unit for varying that number of rotations, n, to n=n+1 when the apparent phase difference $\theta_{2'}$ is determined by the upper area determining unit as falling in the upper area and the next taken-in apparent phase difference $\theta_{2'}$ is determined by the lower area determining unit as falling in the lower area;

a second rotation number varying unit for varying that number of rotations, n, to n=n−1 when the apparent phase difference $\theta_{2'}$ is determined by the lower area determining unit as falling in the lower area and the next taken-in apparent phase difference $\theta_{2'}$ is determined by the upper area determining unit as falling in the upper area; and a measured-information outputting unit for outputting state-measured information of the material corresponding to an angle difference $\Delta\theta$ between the true phase difference $\theta_2$ and the reference phase difference $\theta_1$.

The present apparatus thus arranged varies the number of rotations, n, to n=n+1 when the apparent phase difference $\theta_{2'}$ is determined by the upper area determining unit as falling in an upper area and the next taken-in apparent phase difference $\theta_{2'}$ is determined by the lower area determining unit as falling in the lower area and varies the number of rotations, n, to n=n−1 when the apparent phase difference $\theta_{2'}$ is determined by the lower area determining unit as falling in the lower area and the next taken-in apparent phase difference $\theta_{2'}$ is determined by the upper area determining unit as falling in the upper area. A true phase difference $\theta_2$ is found by multiplying the thus determined number of rotations, n, by an angle 360° and adding the apparent phase difference $\theta_{2'}$ to the product n×360°.

BEST MODE FOR CARRYING OUT THE INVENTION

An explanation will be given below of a phase difference measuring apparatus according to a first embodiment of the present invention as being applied to a microwave densitometer.

Figure 1:
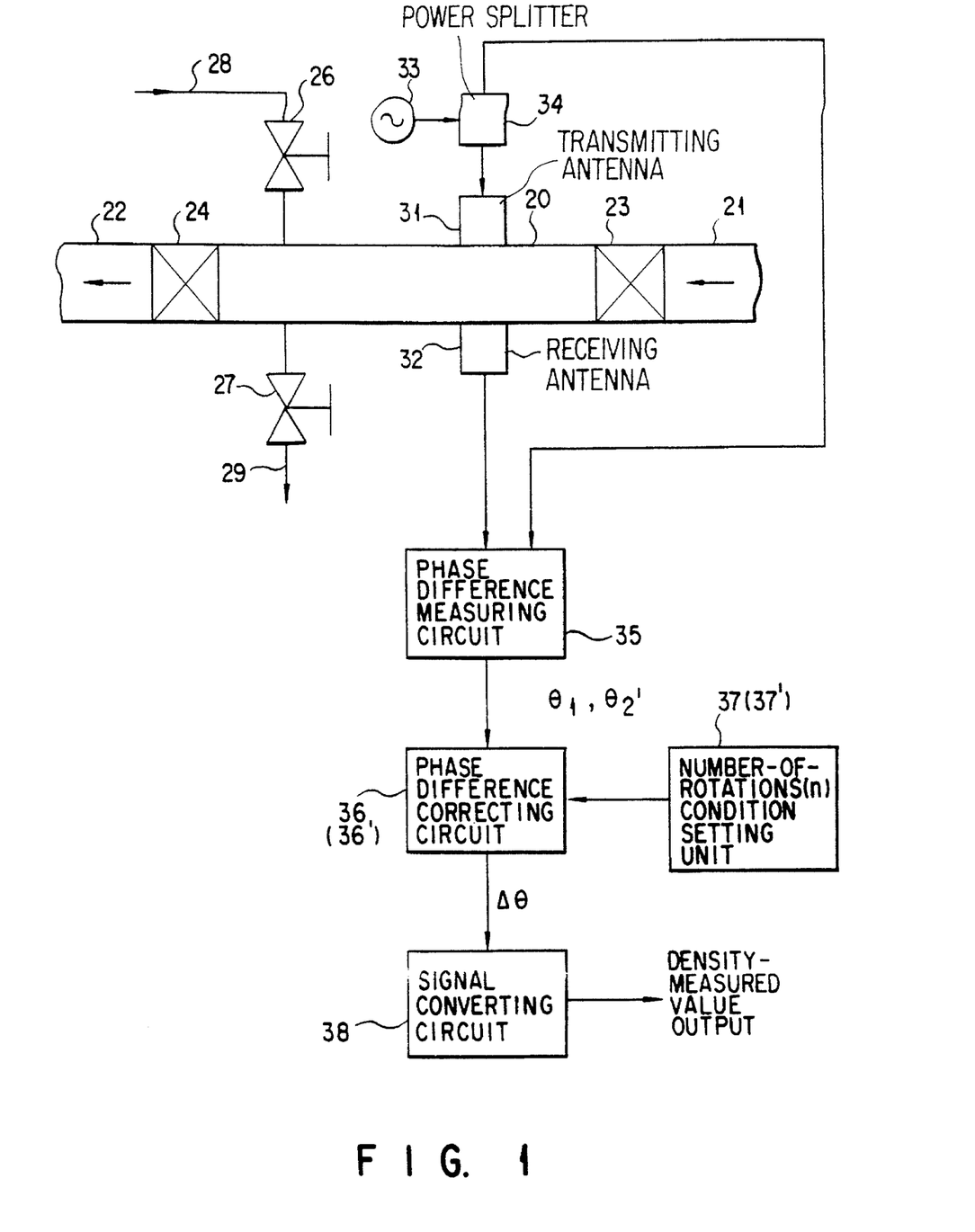
FIG. 1 is a schematic view showing a densitometer according to a first embodiment of the present invention.

FIG. 1 is a schematic view showing a microwave densitometer illustrated in conjunction with the first embodiment of the present invention. The microwave densitometer is provided between an upstream-side tube 21 and a downstream-side tube 22 via interposed partition valves 23 and 24. A water supply valve 26 and water discharge valve 27 are provided at the density detection tube 20. The water supply valve 26 is connected to a water supply tube 28 for conducting a reference fluid, such as tap water from a water service. A water drain tube 29 is connected to the discharge valve 27.

The density detection tube 20 has microwave access windows in those opposed positions with its tube axis as a reference. An antenna mount plate is mounted at the access windows by a hermetically sealing packing. A transmitting antenna 31 and receiving antenna 32 are closely fitted on the antenna mount plate with an insulating material interposed.

A microwave oscillator 33 for emitting a microwave is provided at the transmitting system of the densitometer. An output of the microwave oscillator 33 is transmitted to the transmitting antenna 31 through a power splitter 34.

Figure 2:
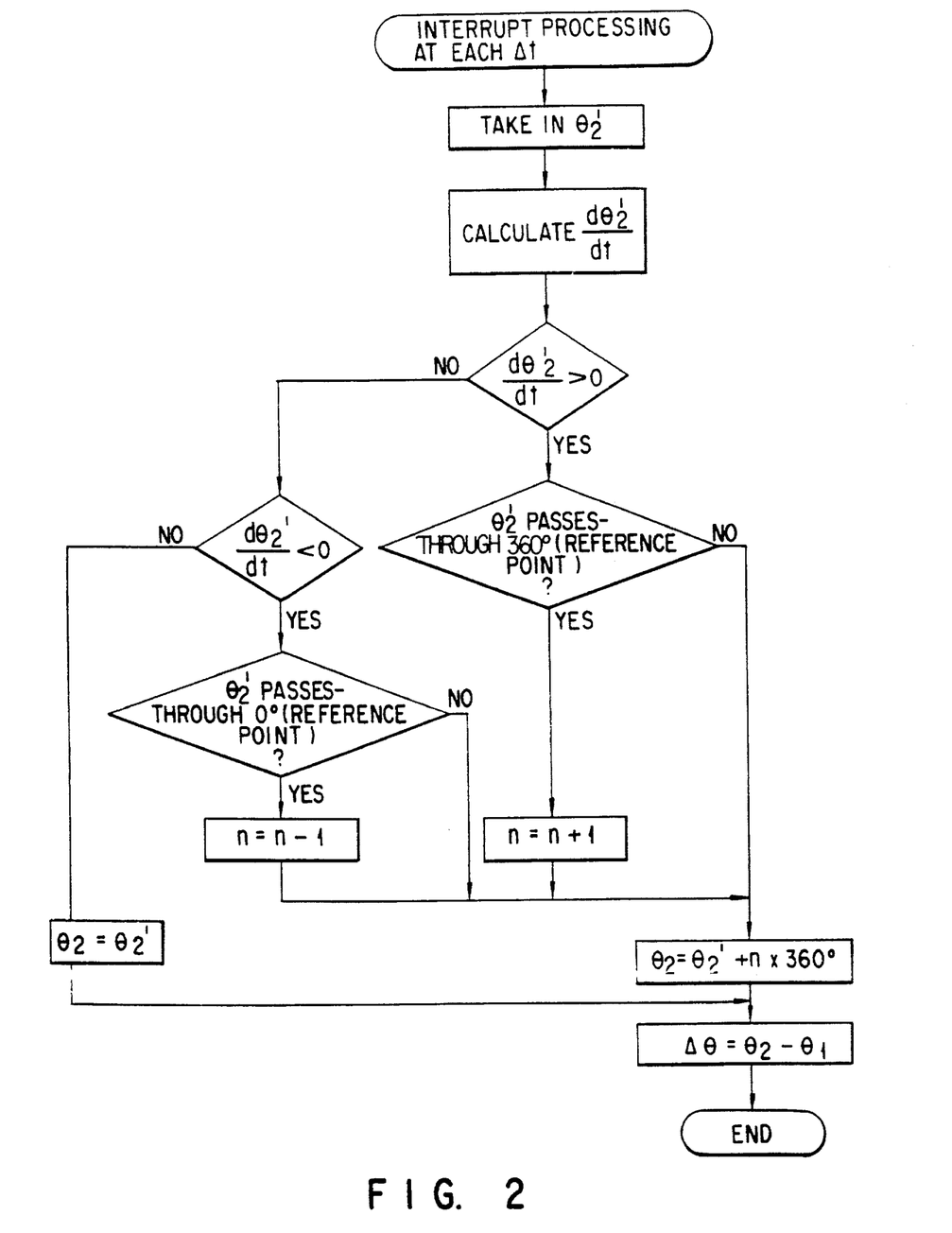
FIG. 2 is a flow chart showing an operation of a phase difference correcting circuit in the densitometer of the first embodiment.
Figure 3:
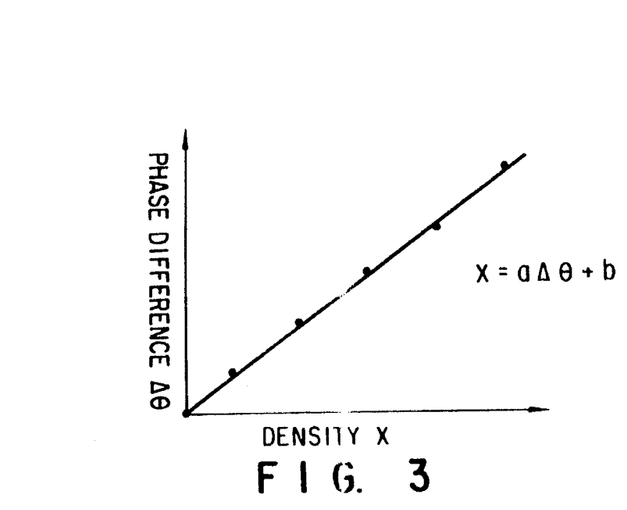
FIG. 3 is a view showing working curve data set to a signal converting circuit in the densitometer of the first embodiment.

The receiving system of the densitometer comprises a phase difference measuring circuit 35, phase difference correcting circuit 36, number-of-rotations condition setting unit 37 and signal converting circuit 38. The phase difference measuring circuit 35 receives, together with a receive wave of the microwave from the receiving antenna, part of a transmit wave of the microwave from the power splitter 34 and measures an apparent phase delay of the receive wave relative to the transmit wave. The phase difference correcting circuit 36 detects a true phase delay from the apparent phase delay through the processing made based on the flow chart shown in FIG. 2 and calculates a phase difference $\Delta\theta$ between the true phase delay and a reference phase delay. The number-of-rotations condition setting unit 37 is used to set the number of rotations, n, at a time when a power supply is turned on and allows the selection of a rotation-of-numbers action mode (a mode 1: the number of rotations just before a power supply OFF, a mode 2: the number of rotations 0) and manual setting of the true number of rotations, n. The signal converting circuit 38 has set working curve data as shown in FIG. 3 and detects, on the basis of the working curve data, a density level corresponding to a phase difference $\Delta\theta$ coming from the phase difference correcting circuit 36 and, being converted to a corresponding current signal, delivers the current signal.

The density measuring operation of the densitometer with the use of the microwave in accordance with the present embodiment thus arranged will explained below.

First, a reference fluid (for example, tap water) of zero concentration is introduced into the densitometer detection tube 20 and a corresponding reference phase delay $\theta_1$ is measured. Here the term "phase delay" is intended to mean a phase delay of the microwave receive wave relative to the microwave transmit wave at the phase difference measuring circuit 35.

Upon measurement of the reference phase delay $\theta_1$, a measuring fluid such as sludge is discharged with the partition valves 23, 24 closed and the water discharge valve 27 opened and then the water supply valve 36 is opened to supply the tap water to allow any stain on the inner surface of the tube 20 to be cleaned and, thereafter, the water discharge valve 27 is closed and the tube 20 is filled with the tap water.

Figure 4A:
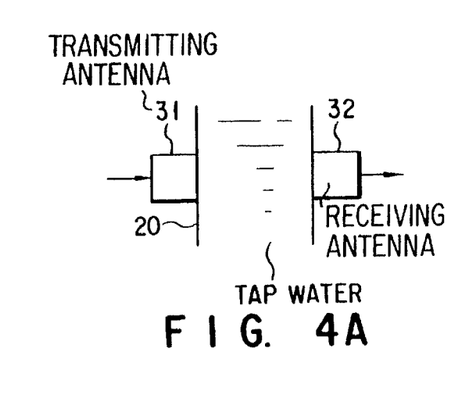
FIG. 4A is a view showing a state in which tap water runs through a density detection tube as a reference point of the density.

After the tap water has been so filled, a microwave signal is generated from the microwave oscillator 33 as shown in FIG. 4A and supplied via the power splitter 34 to the transmitting antenna 31 where it is transmitted and it is received by the receiving antenna 31 after propagating across the tap water in the tube 20. The microwave receive wave is transmitted to the phase difference measuring circuit 35. In this connection it is to be noted that part of the microwave transmit wave is sent to the phase difference measuring circuit 35 from the power splitter 34.

The phase difference measuring circuit 35 compares the microwave transmit wave with the received microwave to measure a reference phase delay $\theta_1$ associated with the reference fluid. The measured reference phase delay $\theta_1$ is sent to the phase difference correcting circuit 36 for storage. An initial value "0" corresponding to the number of rotations n is set, by the setting unit 37, to the phase difference correcting circuit 36.

Figure 4B:
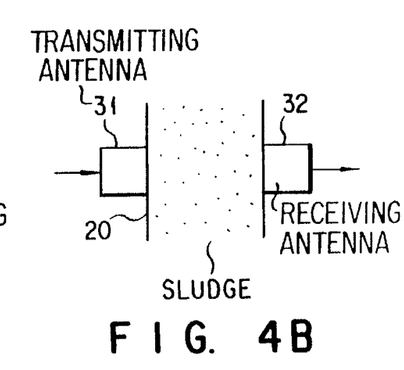
FIG. 4B is a view showing a state in which a measuring fluid runs through a density tube.

Thereafter, the tap water in the tube 20 is discharged with the discharge valve 27 opened and then a measuring fluid containing a to-be-measured material moves there with the partition valves 23 and 24 opened. In this state, a microwave is transmitted from the microwave oscillator 33. The microwave signal, as set out above, is sent via the power splitter 34 to the transmitting antenna 31 and from there to the phase difference measuring circuit 35. The microwave emerging from the transmitting antenna 31 reaches the transmitting antenna 32, as shown in FIG. 4B, after propagating across the fluid in the concentration detection tube 20. Upon the reaching of the microwave, the receiving antenna 32 delivers a microwave signal with a phase delay corresponding to the density of the measuring fluid. The phase difference measuring circuit 35 measures an apparent phase delay $\theta_{2'}$ of a microwave signal with a phase delay corresponding to the density of the measuring fluid. In the state in which the measuring fluid containing the to-be-measured material moves, the microwave is continuously transmitted and an apparent phase delay $\theta_{2'}$ is measured by the phase difference measuring circuit 35 and the corresponding data is sequentially delivered to the phase difference correcting circuit 36.

The detailed processing by the phase difference correcting circuit 36 will be explained below with reference to FIG. 2. At each minute time $\Delta t$, the phase difference correcting circuit 36 receives the apparent phase delay $\theta_{2'}$ from the phase difference measuring circuit 35 and performs the following processing.

That is, the phase difference measuring circuit 35 differentiates the apparent phase delay $\theta_{2'}$ to detect an increase/decrease direction. If $d\theta_{2'}/dt$ is positive, the phase delay $\theta_{2'}$ is increased and it is determined whether or not one rotation is made. That is, if the differentiated value of the apparent phase delay $\theta_{2'}$ is positive and phase delay $\theta_{2'}$ passes through 360°, then an actually measured apparent phase delay $\theta_{2'}$ is observed as falling in a range $0 \leq \theta_{2'} < 360°$. In reality, a true phase delay $\theta_2$ falls in a range $360° \leq \theta_2 < 720°$ and the number of rotations varies from 0 to 1.

If $d\theta_{2'}/dt$ is negative, on the other hand, an apparent phase delay $\theta_{2'}$ is decreased and it is determined whether or not the phase delay passes through 0°. That is, if a differentiated value of the apparent phase delay $\theta_{2'}$ is negative and phase delay $\theta_{2'}$ passes through 0°, the apparent phase delay $\theta_{2'}$ is observed as falling in a range $0 \leq \theta_{2'} < 360°$. Since, on the other hand, an actual phase delay $\theta_2$ falls in a range of $-360° \leq \theta_2 < 0°$, the number of rotations varies from 0 to $-1$ in other words, "n" is changed to (n−1). In this way, that number of rotations is stored as data in a number-of-rotations memory, not shown. The number of rotations is newly updated each time there is a variation in the number of rotations involved.

The true phase delay $\theta_2$ is calculated based on the following equation:

$$\theta_2 = \theta_{2'} + n \times 360° \quad (1)$$

Stated in more detail, when a time differentiated value $d\theta_{2'}/dt$ of the apparent phase delay $\theta_{2'}$ is positive and true phase delay $\theta_2$ exceeds 360° (one rotation) to reach a range 360° to 720°, then $\theta_2 = \theta_{2'} + 360°$. Further, when the time differentiated value $d\theta_{2'}/dt$ of the apparent phase delay $\theta_{2'}$ is positive and true phase delay $\theta_2$ exceeds 720° (two rotations) to reach an angle range of 720° to 980°, $\theta_2 = \theta_{2'} + 720°$.

In a similar way, when the $\theta_{2'}$ time differentiated value $d\theta_{2'}/dt$ is positive and $\theta_{2'}$ exceeds 360° each time, the addition of 360° is made to detect a true phase delay angle $\theta_2$.

When, on the other hand, the time differentiated value of the apparent phase delay $\theta_{2'}$ is negative and true phase delay $\theta_2$ becomes smaller than 0° (-one rotation) to reach an angle range 0° to −360°, $\theta_2 = \theta_{2'} - 360°$.

In a similar way, the $\theta_{2'}$ time differentiated value $d\theta_{2'}/dt$ is negative and $\theta_{2'}$ falls below 0° each time, each addition of −360° is made to detect a true phase delay angle $\theta_2$.

Then a phase difference $\Delta\theta$ between a reference phase delay $\theta_1$ stored upon measurement of the above-mentioned reference fluid and the true phase delay $\theta_2$ calculated by the equation (1) is detected based on the following equation:

$$\text{the phase difference } \Delta\theta = \theta_2 - \theta_1 \quad (2)$$

In a similar way, each time the above-mentioned condition is established the number of rotations, n, is varied to find a true phase delay $\theta_2$ and phase difference $\Delta\theta$.

When the signal converting circuit 38 receives a phase difference $\Delta\theta$ from the phase difference correcting circuit 36, corresponding density is found in accordance with the working curve data representing a density/phase difference relation. The signal converting circuit 38, after converting the density to a corresponding signal, is delivered as an output. If the density measuring range is, for example, 0 to 10%, a corresponding current signal 4 to 20 mA is delivered as an output.

It is to be noted that, when a power supply of the densitometer is turned on once being turned off (or failing), a value corresponding to a predetermined number of rotations is used as an initial value in accordance with a mode which is set to the setting unit 37. If a mode 1 is selected at the setting unit 37, the number of rotations involved is set as the number of rotations, n, before the power supply is turned OFF and, if a mode 2 is selected at the setting unit 37, the number of rotations involved is set as the number of rotations, 0.

Judging from the result of measurement by another density measuring method (off-line measurement by a dry weight method, etc.,) and working condition of a plant with the densitometer provided thereon, it is possible to manually set the number of rotations, n, corresponding to a true phase delay angle $\theta_2$.

With the densitometer of the present embodiment, since the true phase delay $\theta_2$ is calculated by grasping, at all times, the number of rotations to which the true phase delay $\theta_2$ belongs and adding the product of the number of rotations, $n \times 360°$, to the apparent phase delay $\theta_{2'}$, it is possible to obtain an exact, true phase delay $\theta_2$ even if the true phase delay $\theta_2$ becomes above 360° or less than 0°. It is, therefore, possible to measure the density of a high concentration measuring fluid involving, for example, more rotations of the true phase delay $\theta_2$ and hence to make density measurement in a tube of large size.

The present apparatus may be so constructed as to determine whether or not an apparent phase delay $\theta_{2'}$ makes one rotation in a range of −180° to +180°. The rotation of the apparent phase delay $\theta_{2'}$ is determined according to the polarity of a differentiated value of the apparent phase delay $\theta_{2'}$, and to whether or not the apparent phase delay $\theta_{2'}$ passes through +180° or −180°, with +180° or −180° set as a reference point.

For example, if $d\theta_{2'}/dt$ is positive and apparent phase delay $\theta_{2'}$ passes through +180°, the number of rotations, n, is changed to n=n+1. On the other hand, if $d\theta_{2'}/dt$ is negative and apparent phase delay $\theta_{2'}$ passes through −180°, the number of rotations, n, is changed to n=n−1.

In the above-mentioned first embodiment, although the function of the phase difference correcting circuit 36 is realized by a software, it can also be done with a hardware circuit.

Figure 5:
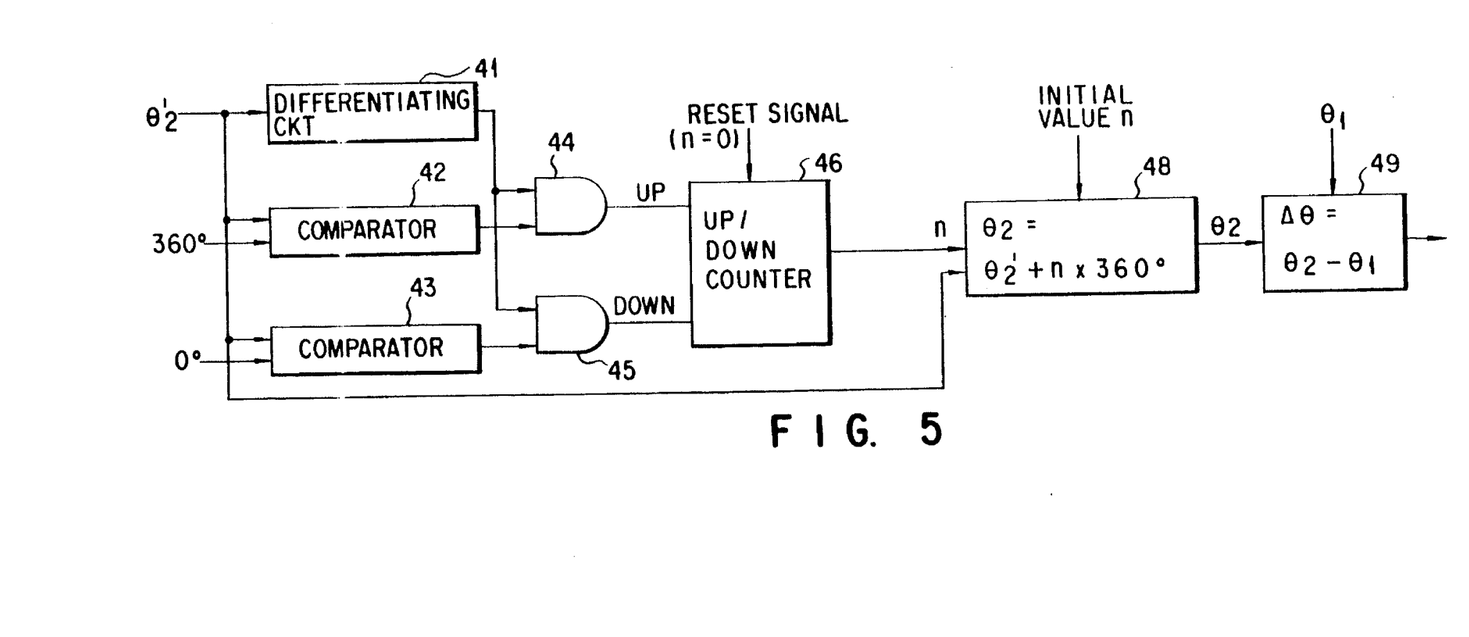
FIG. 5 is a schematic view showing a circuit device composed of a hardwarized phase difference correcting circuit in the densitometer of the first embodiment.

FIG. 5 is a view showing a circuit device with the function of the phase difference correcting circuit 36 realized with a hardware. In this circuit device, an apparent phase delay $\theta_{2'}$ from the phase difference measuring circuit 35 is input to a differentiating circuit 41 and first and second comparators 42 and 43. The differentiating circuit 41 sends a signal representing the positive/negative polarity of a time-differentiated value of the phase delay $\theta_{2'}$ to first and second AND circuits 44 and 45. A threshold value 360° is set to the first comparator 42 so as to detect that the apparent phase delay $\theta_{2'}$ has exceeded 360°. A threshold value 0° is set to the second comparator 43 so as to detect that the apparent phase delay $\theta_{2'}$ has been brought to below 0°. When the apparent phase delay $\theta_{2'}$ varies from 360°, the first comparator 42 delivers a number-of-rotations increasing signal to the first AND circuit 44. When the apparent phase delay $\theta_{2'}$ varies from 0°, the second comparator 43 delivers a number-of-rotations decreasing signal to the second AND circuit 45. When the time-differentiated value of the phase delay $\theta_2$ is positive and number-of-rotations increasing signal is input to the AND circuit 44, then the AND circuit supplies an UP signal as an ANDed signal to an UP terminal of an up/down counter 46. When the time-differentiated value of the phase delay $\theta_{2'}$ is negative and number-of-rotations decreasing signal is input to the second AND circuit 45, then the second AND circuit 45 supplies a down signal as an ANDed signal to a DOWN terminal of the up/down counter 46. In the up/down counter 46, a coincidence is taken between the count output and the number of rotations, n, by resetting the count value of n=0 at a time of making zero adjustment. The up/down counter 46 increments a count value by 1 each time it receives an up signal at its up terminal and decrements a count value by 1 each time it receives a Down signal at its DOWN terminal. A true value calculation circuit 48 is connected to an output terminal of the up/down counter 46 and detects a true phase delay $\theta_2$ through the calculation of the equation (1) above. The output of the true value calculation circuit 48 is input to a subtraction circuit 49 to find A8 through the calculation of the equation (2) above.

A second embodiment of the present invention will be explained below.

The second embodiment includes a functional variant of the phase difference correcting circuit and of the number-of-rotations condition setting unit in the first embodiment above. The second embodiment is similar in its constituent elements to the first embodiment except for the phase difference correcting circuit and number-of-rotations condition setting unit.

Figure 6:
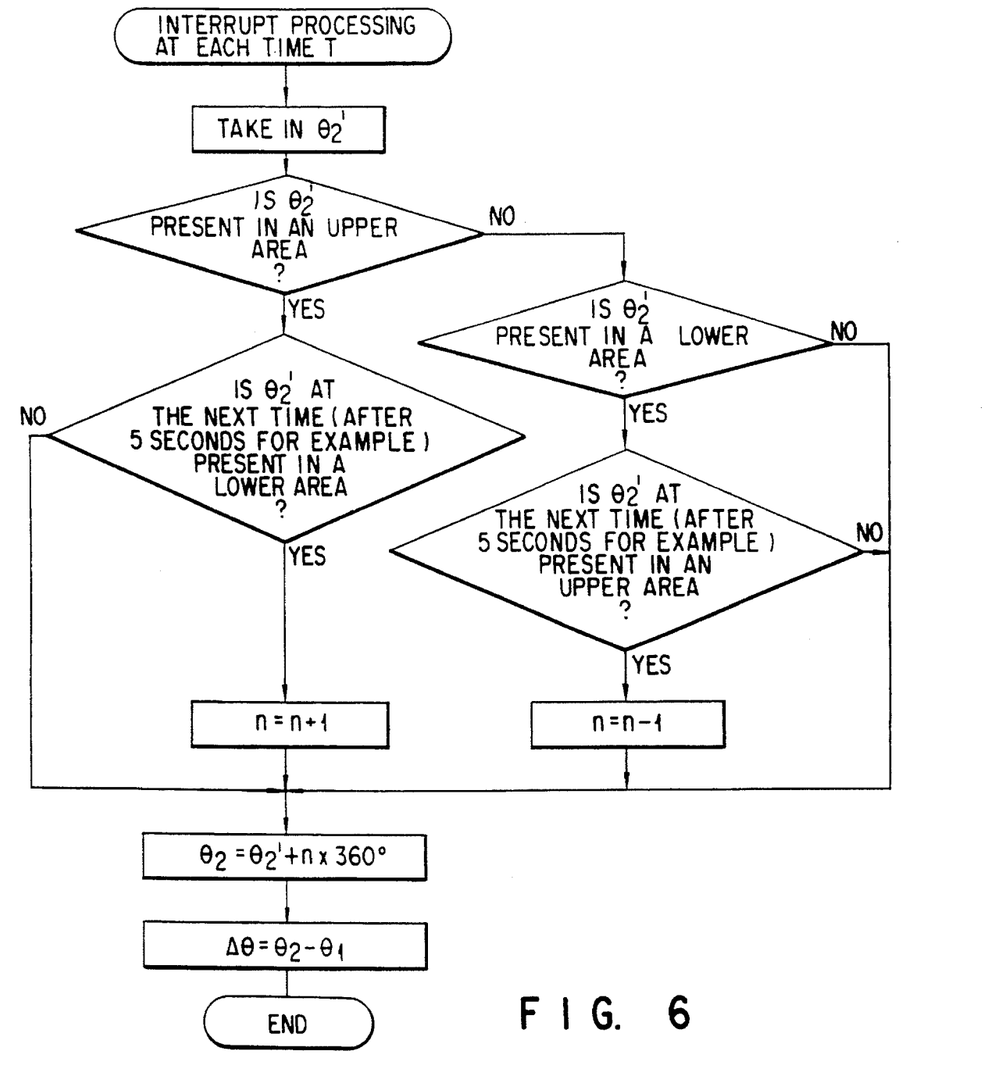
FIG. 6 is a flow chart showing an operation of a phase difference correcting circuit in a densitometer of a second embodiment.

A phase difference correcting circuit 38' (represented by a primed reference numeral to distinguish it from the phase difference correcting circuit 38 in the first embodiment) calculates a true phase delay $\theta_2$ on the basis of a flow chart as shown in FIG. 6. A number-rotations condition setting unit 37' in the second embodiment (represented by a primed reference numeral to distinguish it from the number-of-rotations condition setting unit 37) determines the number of rotations, n, on the basis of a flow chart (FIG. 8) when a power supply is re-thrown ON.

Here, the principle on which a true phase delay $\theta_2$ is calculated at the phase difference correcting circuit 38' will be explained below.

Figure 7:
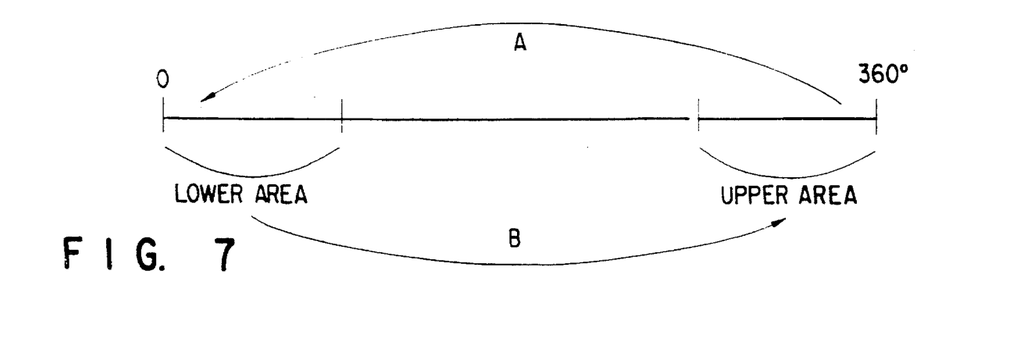
FIG. 7 is a view showing a practical form of the second embodiment where upper and lower areas are set.

An apparent phase delay $\theta_{2'}$ falls in an angle range 0° to 360° as shown in FIG. 7. Over the angle range 0° to 360°, a predetermined area as viewed from 0° toward 360° is set as a lower area and a predetermined area as viewed from 360° toward 0°, as an upper area. According to the present embodiment, an area 240° to 360°, normally an area 260° to 360°, can be set as an upper area, while, on the other hand, an area 0° to 120°, normally an area 0° to 100°, can be set as a lower area.

The apparent phase delay $\theta_{2'}$ is measured not continuously but at a given brief period (a five second interval in this embodiment). In the case where, at a given time, the apparent phase delay $\theta_{2'}$ is present at the upper area and, at the next time, the apparent phase delay $\theta_{2'}$ is present at the lower area, the number of rotations, n, is changed to n=n+1. In the case where, at a given time, the apparent phase delay $\theta_{2'}$ is present at a lower area and, at the next time, the apparent phase delay $\theta_{2'}$ is present at an upper area, the number of rotations, n, is changed to n=n−1. A true phase delay $\theta_2$ is calculated by substituting the number of rotations, n, into the equation (1) above.

The reason that the number of rotations, n, is changed under such condition is because it is assumed that, in a brief time (for example, five seconds) set as the phase delay measuring period, there is no variation (density, temperature, etc., variations) from the upper toward the lower area or from the lower toward the upper area in actual practice when the apparent phase delay $\theta_{2'}$ is present in the same number-of-rotations, n, range (the true phase delay $\theta_2$ is in a range 0° to 360°, for example, at n=0). When, in a five-second period for example, the apparent phase delay $\theta_{2'}$ is varied from the upper toward the lower area or from the lower toward the upper area, it can be determined that the number of rotations, n, has been changed.

The upper and lower areas above and arbitrary rotation number initial value, n, are manually set in the rotation-of-rotations condition setting unit 37' and a high density threshold value Xmax and minus density threshold value Xmin are manually set there. The high density threshold value Xmax is intended to mean a maximum value predictable as a density value of a to-be-measured material or a high value obtainable for the to-be-measured material. The minus density threshold value Xmin is intended to mean a low value not occurring even if, with a reference phase difference $\theta_1$ set to a zero point, there is a drift of the zero point toward a minus side.

In the second embodiment having an arrangement as set out above, like the previous first embodiment, a microwave is transmitted to a standard fluid consisting of tap water and the phase delay $\theta_1$ of a received microwave is measured and stored in the phase difference correcting circuit 36'. The phase difference correcting circuit 36' receives, as read-in data, those upper and lower areas for rotation number determination and a rotation number initial value n=0 from the number-of-rotations setting unit 37'.

Then a microwave is transmitted to a measuring fluid containing a material to be measured and an apparent phase delay $\theta_{2'}$ is measured for a brief time period (for example, five seconds). Each time the apparent phase delay $\theta_{2'}$ is measured, processing is effected on the basis of a flow chart shown in FIG. 6, thus calculating a true phase delay $\theta_2$ and then a phase difference $\Delta\theta$.

That is, the apparent phase delay $\theta_{2'}$ is taken from the phase difference measuring circuit 35 and it is determined whether or not $\theta_{2'}$ is present in the upper area. If, being present in the upper area, it is determined whether or not $\theta_{2'}$ after a lapse of five seconds is present in the lower area. If being so present, since the apparent phase delay $\theta_{2'}$ is varied from the upper toward the lower area, during the five second period, as indicated by A in FIG. 7, the number of rotations, n, is changed to n=n+1.

If $\theta_{2'}$ taken into the phase difference measuring circuit 35 does not belong to the upper area, it is determined whether or not $\theta_{2'}$ is present in the lower area. If being so present, it is determined whether or not $\theta_{2'}$ after a lapse of five seconds is present in the upper area. If $\theta_{2'}$ is present in the upper area, since it is varied from the lower toward the upper area during the five seconds, the number of rotations, n, is varied to n=n−1.

If being otherwise, the variation of rotations that number of n, does not take place.

With the number of rotations, n, so determined, the true phase delay $\theta_2$ is calculated using the above equation (1) and the phase difference $\Delta\theta$ is calculated using the above equation (2).

The condition setting unit 37' takes in the most recent number-of-rotations, n, at all times determined by the phase difference correcting circuit 36' and allows it to be stored in a nonvolatile memory, not shown. Even if a power supply of the densitometer fails or is manually rendered OFF, the setting unit 37' holds the number of rotations, n, just before the power supply is rendered OFF.

Figure 8:
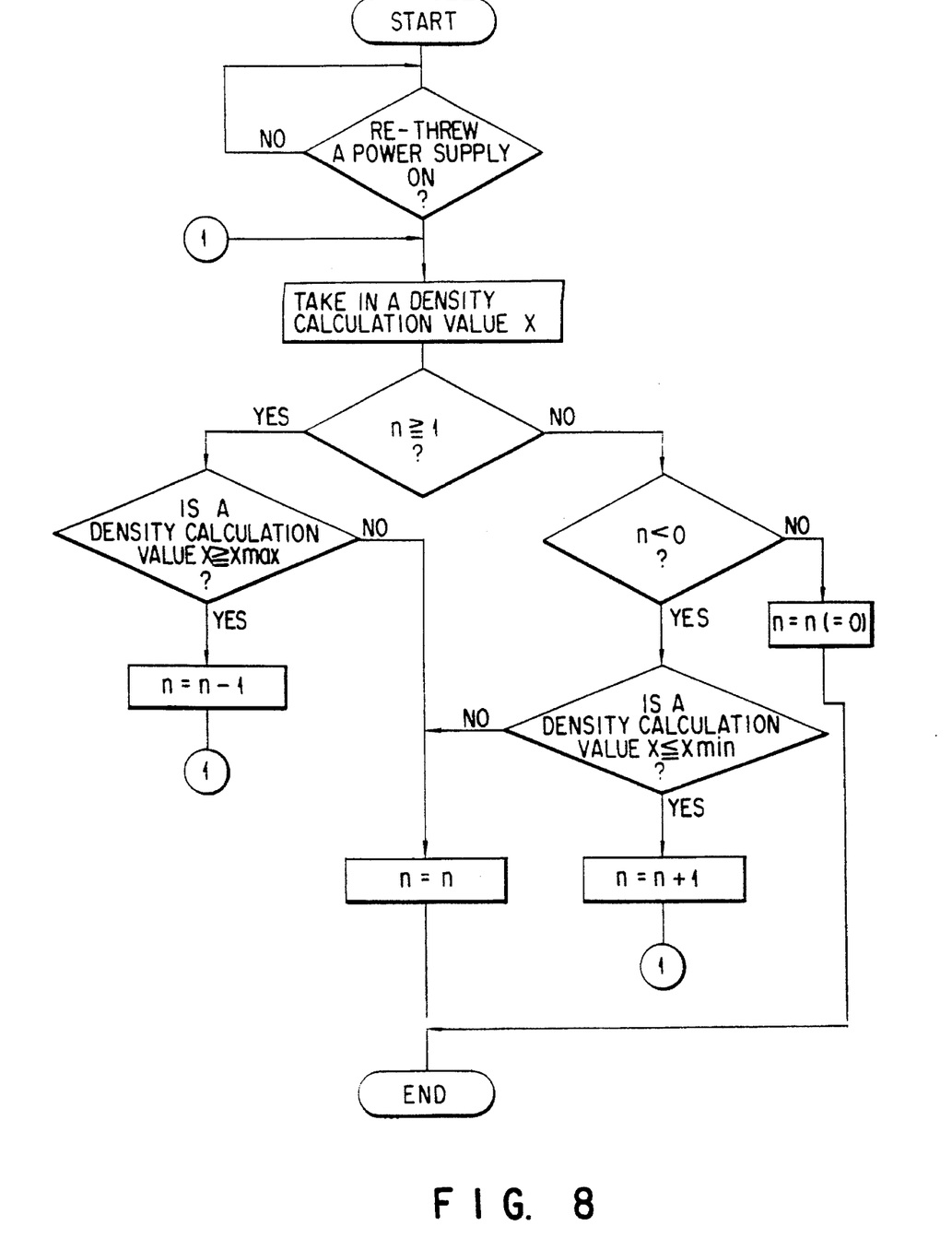
FIG. 8 is a flow chart showing a rotation number initial value setting operation of a number-of-rotations condition setting unit in the second embodiment.

With the power supply of the densitometer re-thrown ON, processing is carried out by the setting unit 37' as shown in FIG. 8 to find an accurate number-of-rotations, n.

That is, with the power supply of the densitometer re-thrown ON, density calculation is made by the phase difference correcting circuit 36' and signal converting circuit 38 with the use of the number-of-rotations, n, (a hold value of the above-mentioned nonvolatile memory) just before the power supply is turned OFF.

With the condition setting unit 37', if the power supply of the densitometer is re-thrown ON, a density calculation value X is taken in as a calculated value obtained with the use of the number-of-rotations, n, just before the power supply is rendered OFF.

Then it is determined whether or not the number-of-rotations, n, just before the power supply is rendered OFF satisfies a condition $\geq 1$. If the number-of-rotations, n, used for density calculation is $n \geq 1$, then comparison is made between the density calculation value X and the high density threshold value Xmax. If $X \geq Xmax$, the number-of-rotations, n, is varied to n=n−1, and, if X<Xmax, no variation of the number-of-rotations, n, is made.

Unless the number-of-rotations, n, just before the power supply is rendered OFF is $n \geq 1$, it is determined whether or not a condition n<0 is satisfied. If n<0, comparison is made between the density calculation value X and the high density threshold value Xmax. For $X \leq Xmin$, the number-of-rotations, n, is varied to n=n+1. For X>Xmin, no variation of the number-of-rotations, n, is made and no variation of the number-of-rotations, n, is made either at n=0.

In the case where the value of the number-of-rotations, n, is evidently varied (for example, when the density is greatly varied between before the power supply is turned OFF and when the power supply is re-thrown ON), any number-of-rotations, n, is manually set from the condition setting unit 37'.

In this way, the determined number-of-rotations, n, is input to the phase difference correcting circuit 36'. With the phase difference correcting circuit 36', subsequent processing is varied by using, as a reference, the number-of-rotations, n, re-set from the condition setting unit 37'.

According to the present embodiment, with the lower and upper areas set in a range 0° to 360°, comparison is made between the present range and the previous range to which the apparent phase delay $\theta_2$, belongs and, by doing so, the number-of-rotations is determined as having been varied. It is, therefore, possible to accurately grasp the number-of-rotations of the apparent phase delay $\theta_2$, and to calculate an accurate phase difference $\Delta\theta$. It is thus possible to, even if the phase delay exceeds one rotation beyond 360°, accurately measure the density of a high density measuring fluid and to accurately do so in a density detection tube of large size.

According to the second embodiment, the high density threshold value Xmax and minus density threshold value Xmin are set to the condition setting unit 37'. Comparison is made between the density calculation value X, on one hand, which, at a time of re-throwing the power supply of the densitometer ON, is calculated with the use of the number-of-rotation, n, just before the turning off of the power supply and the high density threshold value Xmax or minus density threshold value on the other. By doing so it is possible to determine an optimal rotation number corresponding to the density, etc., of the present measuring fluid and to maintain an accurate rotation number even after the power supply of the densitometer has been re-thrown ON.

Although, in the above-mentioned second embodiment, the upper and lower areas may be set in the range 0° to 360°, the number-of-rotations, n, may be determined by setting the upper and lower areas in a range of −180° to +180°. In the case where the phase delay is to be measured in the range of −180° to +180°, a predetermined area in the range of −180° to +180° is set as a lower area as viewed from −180° toward +180° and a predetermined area in the range of −180° to +180° is set as an upper area as viewed from +180° toward −180°.

Although in the above-mentioned second embodiment the function of the phase correcting circuit 36' is realized with a software, the same function can be realized with a hardware circuit.

Figure 9:
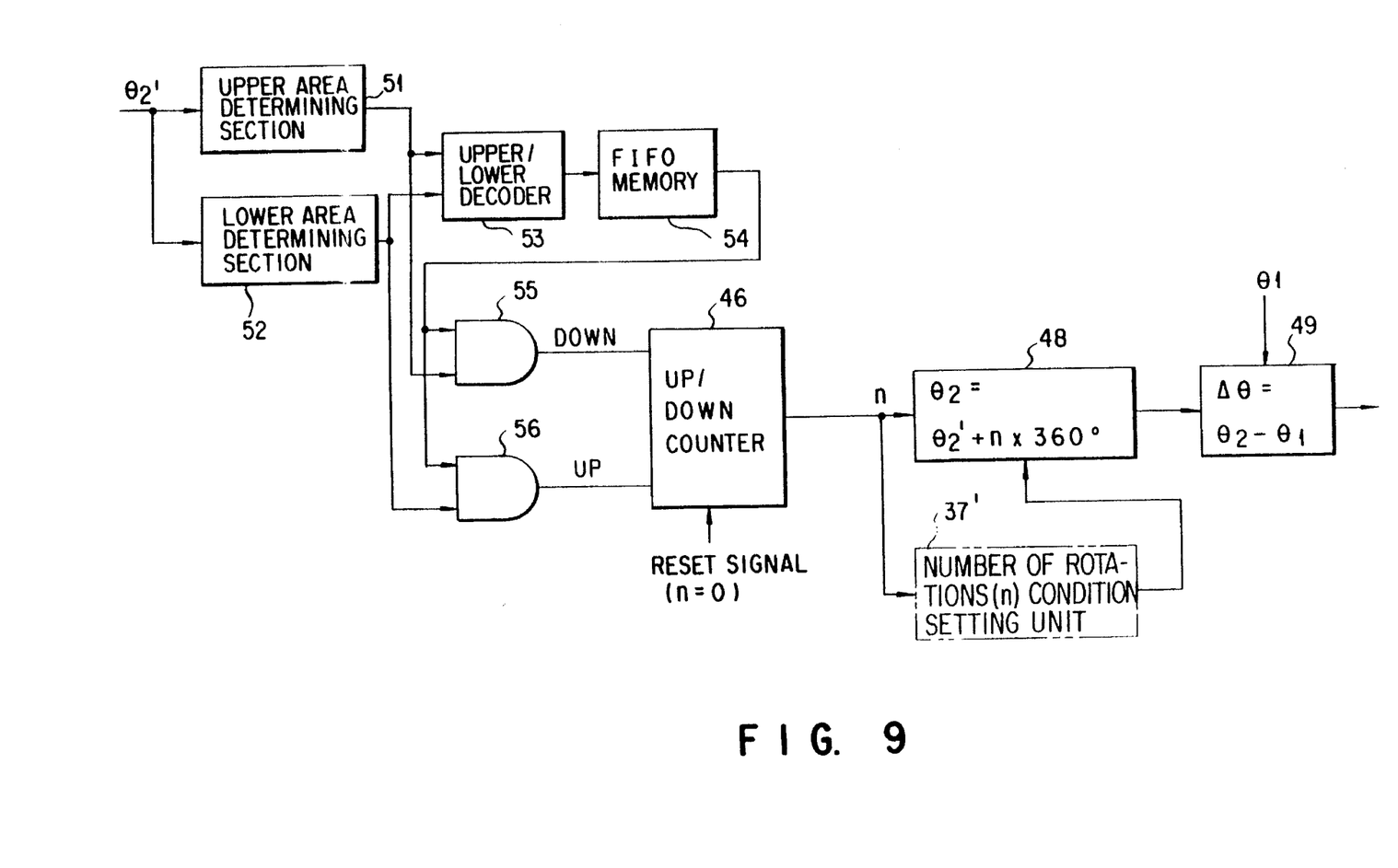
FIG. 9 is a schematic view showing a phase difference correcting circuit in the densitometer of the second embodiment.

FIG. 9 shows an arrangement of a circuit device with the function of the phase difference correcting circuit 36' of the second embodiment realized with a hardware circuit. In this embodiment the same references are employed to designate parts or elements corresponding to those shown in FIG. 5.

In the circuit device, an apparent phase delay $\theta_2$, from the phase difference measuring circuit 35 is input to an upper area determining section 51 and lower area determining section 52. The upper area (for example, 260° to 360°) is set in the upper area determining section 51 and, if the apparent phase delay $\theta_2$, is set in the upper area, the upper area determining section 51 delivers an upper area detection signal as an output. The above lower area (for example, 0° to 120°) is set in the low area determining section 52 and, if the apparent phase delay $\theta_2$, is present in the lower area, the lower area determining section 52 delivers a lower area detection signal as an output. The upper and lower detection signals are input to a decoder 53. The decoder 53 converts the upper area detection signal to data D1, the lower area detection signal to data D2 and an input other than the upper and lower area detection signals to data D3 and delivers a corresponding output to a FIFO memory 54. The FIFO memory 54 stores continued two data items and, receiving an input from the decoder 53, stores it and delivers one-previous data as an output. A first AND circuit 55 delivers a down count signal as an ANDed output of the upper area detection signal and data D2. A second AND circuit 56 delivers an up count signal as an ANDed output of the lower area detection signal and data D1. The circuit arrangement from an up/down counter 46 to a subtractor 49 is the same as that of FIG. 5.

Although in the above embodiment of the present invention applied to the densitometer the suspended material has been explained as being in a flowing state, the present invention may be applied to making density measurement with the material in a stationary state. Although the tap water has been explained as the reference fluid, use may be made of one containing some material of known density. Although the density detection tube 20 has been explained as being sandwiched between the upstream-side tube 21 and the downstream-side tube 22, if a fluid taken-in container, or a bypass tube, is provided on a running distribution tube for example, then the above technique is applicable to this container or bypass tube and this is also included in a range of the present invention.

Although, in the above embodiment, the present invention has been explained as being applied to the densitometer, the present invention can be applied to a light-wave, radio-wave or ultrasonic-wave distance meter for measuring a distance between two points with the use of an electromagnetic wave such as a light, a radio, etc., wave, or a signal wave such as an ultrasonic wave.

A third embodiment of the present invention will be explained below. This embodiment is one applied to the light wave distance meter.

Figure 10:
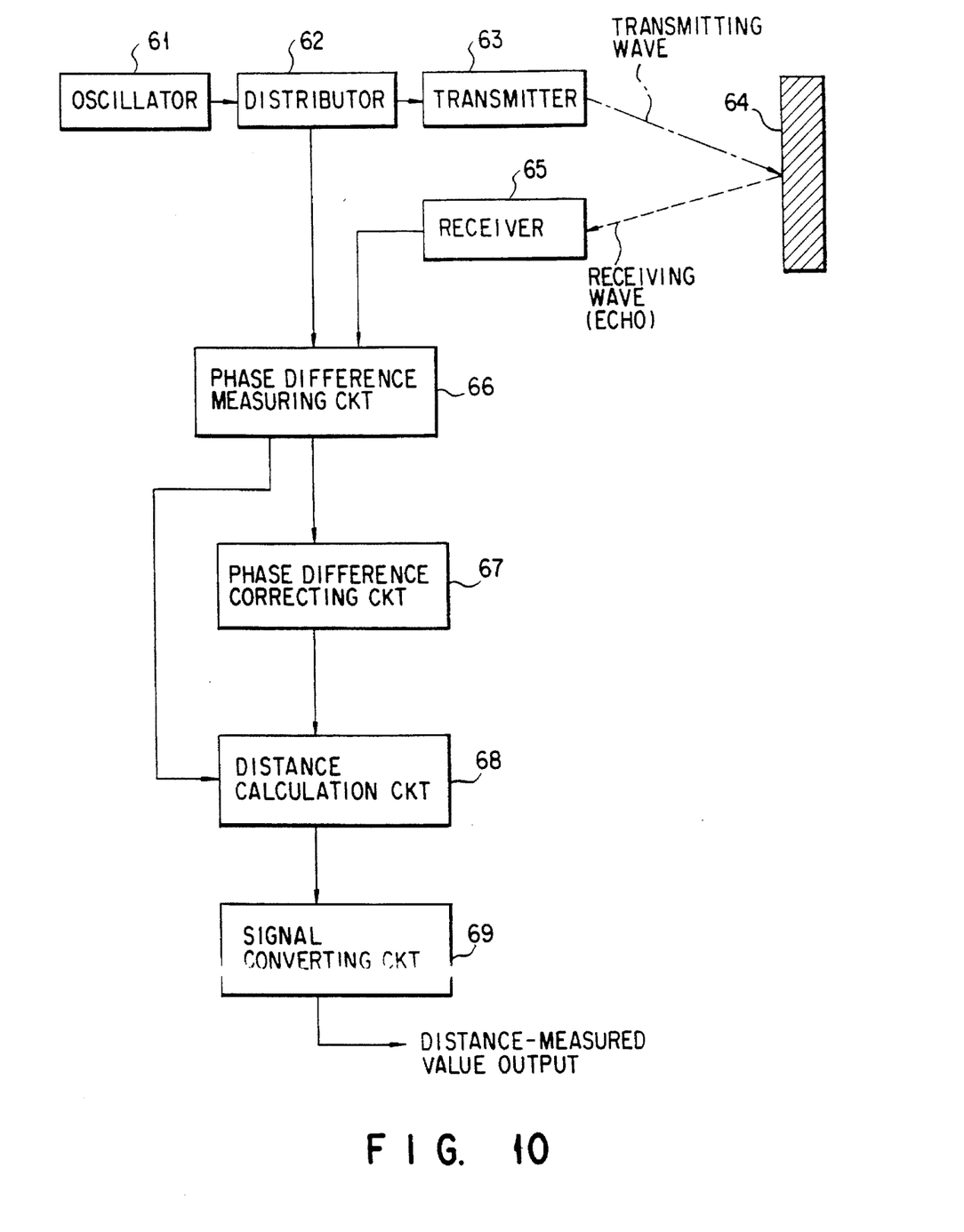
FIG. 10 is a schematic view showing a distance meter according to a third embodiment of the present invention.

FIG. 10 is an arrangement of that light-wave distance meter according to a third embodiment of the present invention.

In the light wave distance meter of the present invention, an oscillation signal which is output from an oscillator 61 set a predetermined oscillation frequency is sent to a transmitter 63 via a distributor 62, the transmitter 63 transmits a wave to an object 64 and a receiver 65 receives a corresponding wave reflected from the object 64 to allow it to be converted to an electrical signal. A phase difference measuring circuit 66 is connected to the output terminal of the receiver 65. The phase difference measuring circuit 66 receives a receive signal from the receiver 65 and a transmit signal from the distributor 62 in the same phase relation to the transmit wave and detects a phase delay of the receive signal behind the transmit signal. A phase difference correcting circuit 67 is connected to an output terminal of the phase difference measuring circuit 66 to perform the same processing as shown in FIGS. 2 or 6 and deliver a resultant phase difference $\Delta\theta$ to a distance calculating circuit 68. The distance calculating circuit 68 stores working curve data as shown in FIG. 14 and finds a moving distance x on the basis of the phase difference $\Delta\theta$ from the phase difference correcting circuit 67 and delivers, as an output, a distance x obtained by adding together the moving distance x and a distance b before movement from the measuring point to the object. A signal converting circuit 69 delivers, as a distance measuring signal, an electric current signal corresponding to the distance X.

The distance measuring operation by this embodiment will be explained below.

Figure 11:
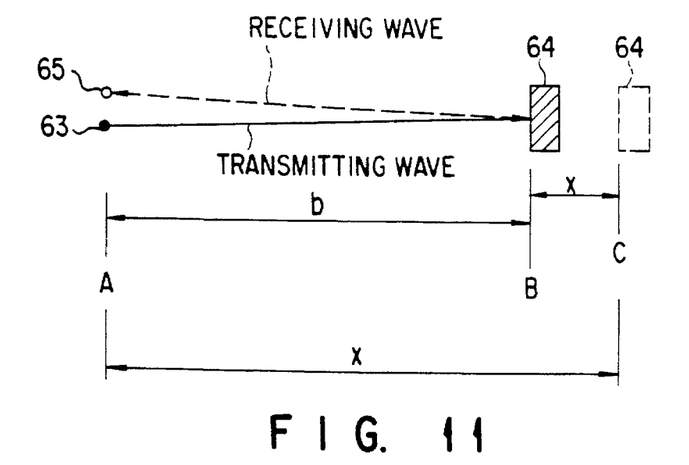
FIG. 11 is a view showing a distance measuring operation of a distance meter according to a third embodiment of the present invention.
Figure 12:
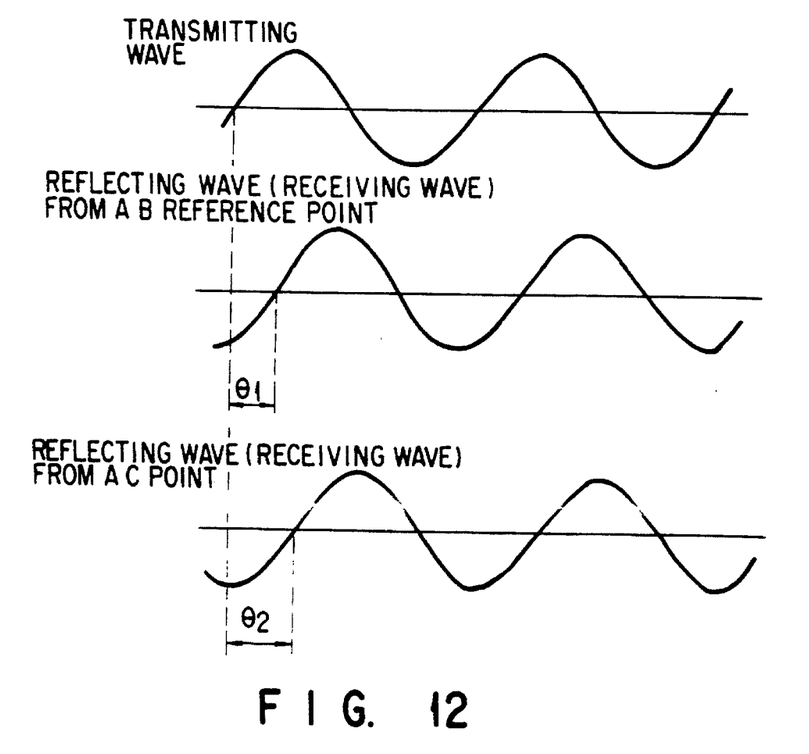
FIG. 12 is a view showing a phase difference between a transmitted wave and a received wave in the third embodiment.

First, an object is placed on a reference point B as shown in FIG. 11, the transmitting signal is sent to the object 64 and a corresponding reflected wave is received by the receiver. As shown in FIG. 12, the phase of the received wave relative to the transmitted wave is shifted by an angle $\theta_1$ in accordance with a distance b between A and B. A reference phase difference $\theta_1$ corresponding to the phase difference between the transmitted wave and the received wave at the reference position B is measured by the phase difference measuring circuit 66 and input to the phase difference correcting circuit 67.

By varying a distance from the point B to the object 64 by sequentially predetermined amounts a phase difference $\theta_{2'}$ between the transmitted wave and the received wave is measured by the phase difference measuring circuit 66 at the respective distances. As shown in FIG. 12, a reflected wave from the object 64 moving to a point C involves a phase difference $\Delta\theta=\theta_2-\theta_1$ relative to a reflected wave from the object 64 at the reference position B. The phase difference correcting circuit 68 at the respective point C is input to the phase difference correcting circuit 68. The phase difference correcting circuit 68 calculates a true phase difference $\theta_2$, given that the number of rotations, n, of the reference phase difference $\theta_1$ at the reference B is set to n=0 and that the phase difference at the respective distance input from the phase difference measuring circuit 66 is placed as an apparent phase difference $\theta_{2'}$. The difference between the true phase difference $\theta_2$ and the reference phase difference $\theta_1$ is calculated and then input to the distance calculating circuit 68.

Figure 13:
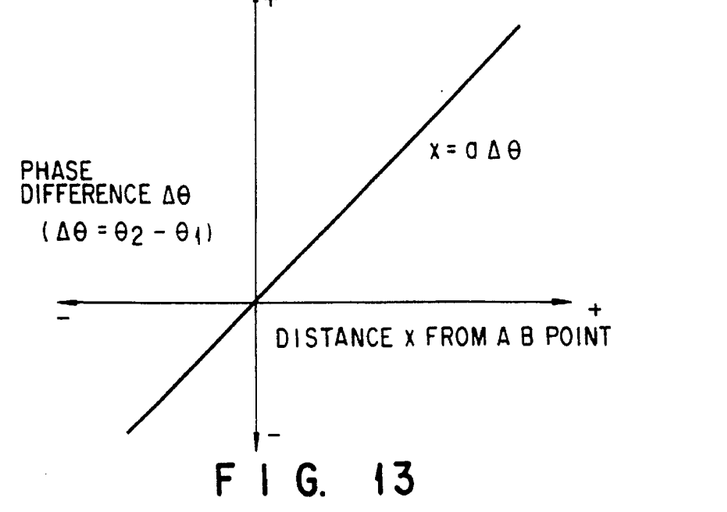
FIG. 13 is a view showing working curved data set in a distance calculating circuit of the distance meter of the third embodiment.

The distance calculating circuit 68 finds a relation between the distance x from the reference position B and a phase difference $\Delta\theta$ $(=\theta_2-\theta_1)$ and determines a working curve $X=a\Delta\theta$ relating to the moving distance x shown in FIG. 13 to allow it to be stored therein.

After such preparation has been made, a normal operation is done for measuring a distance constantly varying from the point A to the object 64.

In the distance measuring operation, the phase difference, to the transmitted wave, of the received wave from the position C after movement, is measured as an apparent phase difference $\theta_{2'}$ at the phase difference measuring circuit 66. In the phase difference correcting circuit 66, a true phase difference $\theta_2$ is found from the apparent phase difference $\theta_{2'}$ from the phase difference measuring circuit 66 by processing based on in FIG. 2 or FIG. 6 and calculates a phase difference $\Delta\theta$.

The distance calculating circuit 68, receiving the phase difference $\Delta\theta$ from the phase difference correcting circuit 66, finds a distance x from the reference position B through the calculation of $x=a\Delta\theta$. Further, a distance b from the point A to the point B is added to the distance x to calculate a distance X from the point A to the object 64.

The distance X thus calculated is converted by the signal converting circuit 69 to an electric signal.

In the case where, according to the present embodiment, a distance up to the object 64 is to be measured based on the phase difference between the wave transmitted to the moving object 64, and its received wave, it is possible to accurately measure the distance X even if the phase difference between the transmitted wave and the received wave is varied above 360°.

Although the present invention has been explained as being applied to the light wave distance meter, it can be applied to the radio wave distance meter or ultrasonic wave distance meter on the same principle as that of the light wave distance meter.

Although the present invention has been explained as being applied to the densitometer or the distance meter, it can be applied to other kinds of apparatuses for measuring a physical amount or chemical amount through the utilization of the phase difference.

I claim:

1. A microwave densitometer for measuring a density or concentration of fluid to be measured based on a phase delay of a microwave passed through the fluid, comprising:

a measuring tube through which the fluid flows;

a microwave generator for generating a microwave;

a microwave transmitter for transmitting the microwave supplied from said microwave generator to the fluid flowing in said measuring tube;

a microwave receiver, at an opposite side of the measuring tube as said microwave transmitters for receiving the microwave transmitted from said microwave transmitter through the fluid;

phase difference detecting means for detecting an apparent phase difference $\theta_{2'}$, between the microwave generated by said microwave generator and the microwave received by said microwave receiver when said fluid flows through said measuring tube;

phase difference correcting means for adding the apparent phase difference $\theta_{2'}$ to a product of a number of rotations "n" which is a number of times the apparent phase difference $\theta_{2'}$ passes through a reference point and an angle of 360°, to obtain a true phase difference $\theta_2$ corresponding to a density or concentration of said fluid, the reference point constituting one angle in a variation range of the apparent phase difference $\theta_{2'}$;

tendency detecting means for continuously detecting a direction in which the apparent phase difference $\theta_{2'}$ is increased or decreased;

means for varying the number of rotations "n" to n=n+1 when the apparent phase difference $\theta_{2'}$ detected by the tendency detecting means is passing through the reference point while increasing;

means for varying the number of rotations "n" to n=n−1 when the apparent phase difference $\theta_{2'}$ detected by the tendency detecting means is passing through the reference point while decreasing;

select means for selecting either of a first mode using the number of rotations "n" immediately before a power supply is turned off upon calculation of the true phase difference $\theta_2$ immediately after the power supply is re-thrown ON and a second mode using the number of rotations "n" of n=0;

manual setting means for manually setting any number of rotations "n" for said phase difference correcting means; and signal converting means for converting a difference value $\Delta\theta$ into a concentration signal indicating the density or concentration of said fluid, said difference value $\Delta\theta$ indicating a difference between the true phase difference $\theta_2$ and a reference phase difference $\theta_1$ corresponding to a phase difference between the microwave generated by said microwave generator and a microwave received by said microwave receiver when a reference fluid flows in said measuring tube.

2. A method for measuring a density or concentration of fluid, comprising the steps of:

transmitting a first microwave through a reference fluid;

receiving a first reception signal resulting from the first microwave passing through the reference fluid;

calculating a reference phase difference $\theta_1$ on the basis of a phase difference which the first microwave has before and after passage through the reference fluid;

transmitting a second microwave through a fluid to be measured, said second microwave being equal in frequency to the first microwave;

receiving a second reception signal resulting from the second microwave passing through the fluid to be measured;

calculating an apparent phase difference $\theta_{2'}$ on the basis of a phase difference which the second microwave has before and after passage through the fluid to be measured;

calculating a true phase difference $\theta_2$ by adding the apparent phase difference $\theta_{2'}$ to a product of an angle of 360° and a number of rotations "n" which represents a number of times the apparent phase difference $\theta_{2'}$ passes through a reference point, said reference point being represented by an angular value which is within a variation range of the apparent phase difference $\theta_{2'}$;

continuously detecting a direction in which the apparent phase difference $\theta_{2'}$ increases or decreases;

changing the number of rotations "n" to n=n+1 when the apparent phase difference $\theta_{2'}$ is detected as having passed through the reference point while increasing;

changing the number of rotations "n" to n=n−1 when the apparent phase difference $\theta_{2'}$ is detected as having passed through the reference point while decreasing;

selecting one of a first mode and a second mode, said first mode being a mode in which the number of rotations "n" immediately before a power supply is turned off is used when the true phase difference $\theta_2$ is calculated immediately after the power supply is turned on, and said second mode being a mode in which the number of rotations n=0 is used when the true phase difference $\theta_2$ is calculated immediately after the power supply is turned on; and manually setting an initial number of rotations "n".

* * * * *